United States Patent [19]
Lindhofer et al.

[11] Patent Number: 5,985,276
[45] Date of Patent: Nov. 16, 1999

[54] DESTRUCTION OF CONTAMINATING TUMOR CELLS IN STEM CELL TRANSPLANTS USING BISPECIFIC ANTIBODIES

[75] Inventors: Horst Lindhofer, Gröbenzell; Helge Menzel; Hans-Jochem Kolb, both of München; Stefan Thierfelder, Eichenau, all of Germany

[73] Assignee: GSF Forschungszentrum fur Umwelt und Gesundheit GmbH, Oberschleissheim, Germany

[21] Appl. No.: 08/922,966

[22] Filed: Sep. 3, 1997

[30] Foreign Application Priority Data

Sep. 3, 1996 [DE] Germany ............. 196 35 743
Nov. 27, 1996 [DE] Germany ............. 196 49 223

[51] Int. Cl.$^6$ .............. A61K 39/395; C07K 16/28; C07K 16/30
[52] U.S. Cl. ................. 424/136.1; 424/174.1; 424/130.1; 424/133.1; 424/138.1; 424/144.1; 424/154.1; 424/155.1; 435/1.1; 435/2; 530/387.3; 530/387.7; 530/388.75; 530/388.8; 530/388.85
[58] Field of Search ............. 424/133.1, 136.1, 424/138.1, 174.1, 130.1, 144.1, 154.1, 155.1; 435/1.1, 2; 530/387.3, 387.7, 388.75, 388.8, 388.85

[56] References Cited

U.S. PATENT DOCUMENTS 5,320,942  6/1994  Vio Quananta .

FOREIGN PATENT DOCUMENTS 0 637 593 A1  2/1995  European Pat. Off. .

OTHER PUBLICATIONS

Chen, J. et al. *Clinical Cancer Research* (Nov. 1995) 1: 1319–1325.
Silla, L.M.R. et al. *British Journal of Haematology* (1995) 89: 712–718.
Weiner, L.M. et al. *Journal of Hematotherapy* (1995) 4:453–456.
Weiner, G.J. et al., *Leukemia and Lymphoma* (1995) 16: 199–207.
Weiner, G.J. et al. *Journal of Immunology* (1994) 152: 2385–2392.
Kaneko, T. et al. *Blood* (Mar. 1, 1993) 81(5): 1333–1341.
Kaneko, T. et al. *Leukemia and Lymphoma* (1994) 14: 219–229.
Kaneko, T. et al., *Bone Marrow Transplantation* (1994) 14: 213–217.
Lindhofer, H. et al. *26th Annual Meeting of the International Society for Experimental Hematology* Cannes, France, (Aug. 24–28, 1997) 25(8): 879.
Lindhofer, H. et al. *Blood* (Dec. 15, 1996) 88(12): 4651–4658.
B. Alberts et al., "The Functional Properties of Antibodies," *Molecular Biology of The Cell*, Garland Publishing, Inc., p. 965.
M. Balzar et al., *Molecular and Cellular Biology* (Aug. 1998) 18(8): 4833–4843.
H. Jacobs, *Immunology Today* (Dec. 1997) 18(12): 565568.

*Primary Examiner*—Nancy A Johnson
*Attorney, Agent, or Firm*—Townsend and Townsend and Crew LLP

[57] ABSTRACT

The present invention discloses a procedure for the destruction of contaminating tumor cells in stem cell transplants ex vivo using intact bispecific antibodies.

10 Claims, 1 Drawing Sheet

The role of accessory cells in the tumor immunotherapy by means of bispecific antibodies.

DESTRUCTION OF CONTAMINATING TUMOR CELLS IN STEM CELL TRANSPLANTS USING BISPECIFIC ANTIBODIES

BACKGROUND OF THE INVENTION

The invention relates to the ex vivo destruction of contaminating tumor cells in stem cell transplants using intact bispecific antibodies.

With about 43,000 new cases/year, breast cancer occupies a top position in the cancer statistics of women in Germany. Less than one third of the women suffering from lymph node invasion at the time of diagnosis survive for 10 years without relapse.

Against this background, attempts have been made since several years towards the prolongation of life or even healing of female patients suffering from extensive lymph node invasion and distant metastases by means of autologous bone marrow and stem cell transplantation in connection with high-dose chemotherapy. Despite high response rates to the high-dose chemotherapy a permanent cure in the metastatic stage rarely occurs.

Today, the therapy of metastasized mammary carcinoma is almost exclusively a palliative therapy. Clinical phase 1studies were able to show that high-dose chemotherapy (HD-CT) followed by autologous bone marrow or stem cell trans-plantation (aPBSZT) is able to achieve complete remission in female patients with chemotherapy-sensitive metastasized mammary carcinoma. However, the remissions are limited in time and in most of the cases recidivism occurs. The recurrence may arise from clonogenic tumor cells which were reinfused by the transplant and/or from those which have survived the HD-CT in the patient. Micrometastases can be detected in bone marrow after chemotherapy using the sensitive RT-PCR for CK19 or Ep-CAM, respectively, for example C215, and by immunocytology. They are accompanied by an unfavorable prognosis even after HD-CT and autologous stem cell transplantation. Therefore, it seems neccessary to develop new concepts for the elimination of minimal residual disease (MRD) and for the purification of transplants from contaminating tumor cells. Presumably, upon achievement of a remission, the MRD consists mostly of tumor cells being resistant against antiproliferative chemotherapy by remaining in a resting state (kinetic resistance) or by developing biochemical mechanisms such as multi-drug resistance (MDR).

An essential problem in autologous stem cell transplantation is the contamination of the transplant by tumor cells which later may contribute to the occurence of a recidivism in the patient. To date mainly "purging" by immunomagnetic beads has been used for the purification of stem cell transplants from contaminating tumor cells. By this technique, tumor cells are caught on a magnet by bound antibodies carrying iron and, thus, removed from the transplant. However, the time involved and the high technical effort coupled to high costs (approx. 20,000.-DM/patient) are disadvantageous. Moreover, following this in vitro reduction of the number of residual tumor cells a recidivism still may occur—albeit after a delay. The reason for this may be the restriction of the method to the stem cell transplant as well as tumor cells escaping a mechanistic approach such as this for example by "aggregation with normal cells".

For these reasons, other immunological approaches to purify the stem cell transplant were tested such as the addition of activated T cells in combination with bispecific F(ab')2 fragments to redirect T cells to the tumor cells in vitro. It turned out that by such purging hematopoietic stem cells are not affected in their function—as measured in proliferation assays—but the ability to kill tumor cells in these experiments was relatively limited (1–2 log tumor reduction). Also, the use of preactivated T cells cultivated for two weeks has to be regarded as a disadvantage of this approach forcing up the effort and hampering clinical application.

SUMMARY OF THE INVENTION

It is an object of the present invention to provide a novel method for the reduction of the number of contaminating tumor cells in stem cell preparations avoiding the disadvantages known from the prior art.

According to the invention, this object has been achieved by the procedure characterized in claim 1. Preferred embodiments are obvious from the dependent claims and the following specification together with the Examples.

BRIEF DESCRIPTION OF THE DRAWING

The accompanying Figure serves to further illustrate the invention.

DESCRIPTION OF THE PREFERRED EMBODIMENTS

Figure 1:
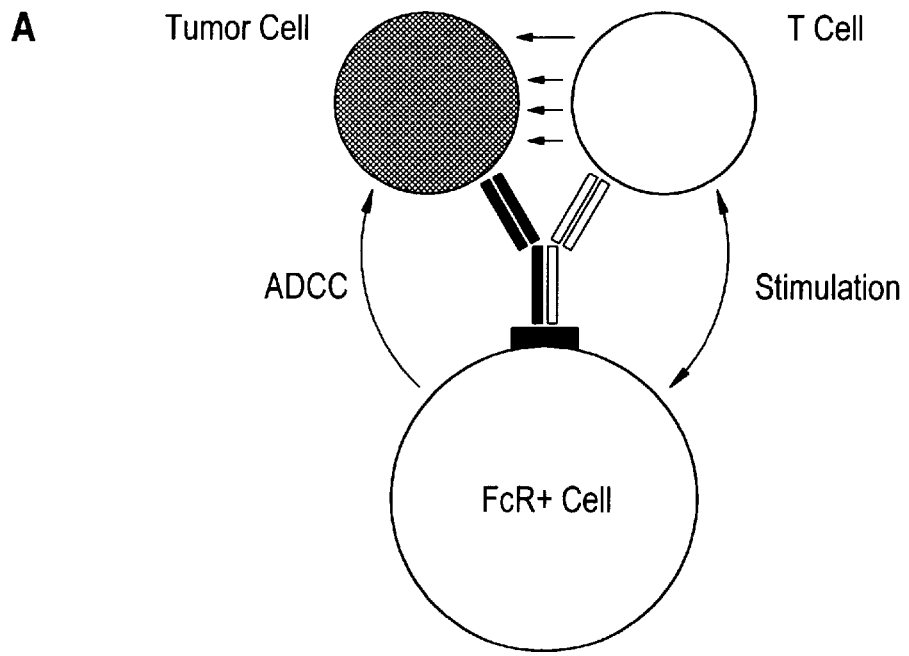
FIGS. 1A and 1B show the role of accessory cells in immunotherapy of tumors by means of bispecific antibodies (ADCC=antibody-dependent cell-mediated cytotoxicity).
Figure 1:
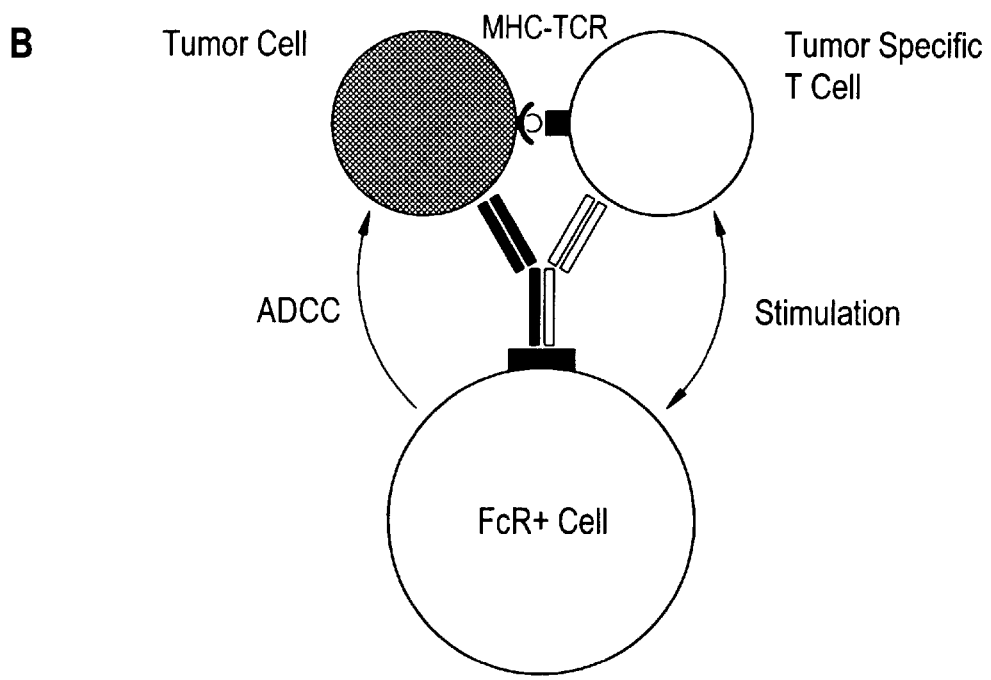

Bispecific antibodies are able to bind to the T cell receptor complex of the T cell with one binding arm and to tumor-associated antigens on the tumor cell with the second binding arm. Thereby, they activate T cells which kill tumor cells by releasing cytokines. Moreover, there is the possibility that T cells recognize tumor-specific antigens via their receptor during activation by bispecific antibodies and that, thereby, a long-lasting immunization is initiated. Of particular importance in this regard is the intact Fc portion of the bispecific antibody which mediates the binding to accessory cells such as monocytes/macrophages/dendritic cells and causes these cells to become cytotoxic themselves and/or at the same time to transduce important co-stimulatory signals to the T cell (see FIG. 1).

In contrast to the prior art, according to the invention there are used intact bispecific antibodies. Intact bispecific antibodies are composed of two antibody semi-molecules (one H and one L immunoglobulin chain each) each representing a specificity, and in addition have like normal antibodies a Fc portion performing the well-known effector functions. They are preferably prepared using the quadroma technology. This method of preparation is exemplified in DE-A-44 19 399. For complete disclosure this document is incorporated in its entirety by reference. It should be understood that other methods of preparation are also useful if they lead to the intact bispecific antibodies according to the above definition required according to the invention.

In the method of the invention, contaminating tumor cells in stem cell preparations (products of leucophoresis) are eliminated in vitro by means of bispecific antibodies (such as anti-CD3 X anti-c-erbB-2, anti-CD3 X anti-Lewis Y, and anti-CD3 X anti-Ep-CAM, for example anti-CD3 X anti-C215). Contacting the bispecific antibodies and the stem cells with the contaminating tumor cells is done under conditions that allow for binding of the bispecific antibodies to the tumor cells and the T cells as well as maintenance of the viability of the stem cells. To keep these parameters is necessary for the survival and the vitality of the stem cells and also of the lymphocytes. For example, the stem cell transplant (product of leucophoresis) is incubated for approximately 4–72 hours, preferably 24–48 hours, with bispecific antibodies at room temperature and a cell density of 30,000–75,000 cells/$\mu$l, preferably 30,000–50,000 cells/$\mu$l with gentle shaking. With a total cell number of approx. $10 \times 10^9$ cells/stem cell transplant, an amount of bsAb of 100–500 $\mu$g is sufficient to kill the tumor cells. A further important point in the procedure of the invention is the use of so-called intact bispecific antibodies. These antibodies are not only able (due to the specificities employed herein) to direct T cells to tumor cells but due to the effector function of the Fc portion are also suitable to kill the tumor cells by complement-mediated lysis or by binding of Fc receptor-positive cells such as macrophages, monocytes or activated neutrophil granulocytes. Thus, by intact bsAb several mechanisms for tumor cell destruction can be activated at the same time.

The intact bispecific antibodies used in the present invention carry a functional Fc part. Contrary to bispecific F(ab)2 fragments which do not include a funtional Fc part the intact bispecific antibodies of the present invention are able to bind not only to T cells but also accessory cells which are also known as Fc-receptor positive cells (e.g. monocytes, macrophages, dendritic cells). The binding of the cells plays an essential role in providing an efficient direct tumor destruction which is 10–1000 times higher compared to the efficiency of the method used by Kaneko et al. The intact bispecific antibodies of the present invention enable an optimal co-stimulation of T cells directed to the antibodies by the accessory cells. In particular responsible for this optimal co-stimulation are surface antigens like CD40, B-7.1, B-7.2, LFA-3 and particular secreted cytokines (like IL-2, IL-6, IL-12, TNF-alpha).

By using the intact bispecific antibody of the present invention an efficient direct destruction of tumor cells by T cells is obtained and furthermore an immune response against the tumor is started. The accessory cells bound by the intact bispecific antibody of the present invention are stimulated to uptake, process and present parts of the tumor. These steps initiated by the use of the bispecific intact antibodies of the present invention are essentially responsible for the induction of a humoral and cellular immune response.

By using the intact bispecific antibodies in the method of the present invention not only a quantitive effect is obtained but also a new quality regarding the induction of an immune response against the tumor.

By using the intact bispecific antibodies of the present invention neither additional cytokines like IL-2 used for a pre-treatment of T cells nor a long lasting cultivation of these cells for at least two weeks is necessary. The cultivation of T cells has to-be conducted under particular conditions (GMP conditions) which are very costly and have to be done under authorization of Paul Ehrlich Institute or FDA. Cultivating of T cells under GMP conditions is not necessary in the present method. At present no other method is available to obtain an efficient destruction of tumor cells in stem cell transplants.

EXAMPLE

For a quantification of the effectivity of intact bsAb in tumor cell killing the leucophoresis products ($10^8$ cells) of a normal donor (see Table 1, Donor 2) and of two leukemia patients were mixed with a defined amount (0.1%) of tumor cells (mammary carcinoma cell line MCF-7). After incubation for 48 h of each of the cellular mixtures with 4 $\mu$g of bsAb (or no antibody or an equimolar amount of the original parental antibodies, respectively) at room temperature and a cell density of 50,000 cells/$\mu$l with gently shaking the cells were plated in different cell densities into 96 well ($10^5$ cells/well) and 24 well ($3 \times 10^6$ or $10^6$ cells/well, respectively) NUNC®cell culture flat bottom plates. After a culturing period of 2 weeks it could be observed that the bsAb was able to reduce tumor cell growth by a factor of 1,000–10,000 (log 3–4) based on the number of tumor cell colonies/plated cells. The result of the tumor colony growth assay (colonogenic A) is summarized in Table 1.

TABLE 1

Tumor colony growth assay

| Plate | No antibody | Parental antibodies C215, anti-CD3 | Bispecific antibody BiUII anti-CD3XC215 | Tumor cells/MNCs/well (= 0.1%) |
|---|---|---|---|---|
| Patient 1 | | | | |
| 24 | 6/6[a] | n.d. | 0/6 $\Sigma = 1.8 \times 10^7$ | 3000/3 × 10e6 |
| 24 | 6/6 | n.d. | 0/6 | 1000/10e6 |
| 96 | 12/12 | n.d. | 0/12 | 500/5 × 10e5 |
| 96 | 10/12 | n.d. | 0/12 | 100/10e5 |
| Tumor reduction: | — | | >4 log | |
| Donor 2 | | | | |
| 24 | 6/6 | | 0/6 $\Sigma = 3 \times 10^7$ | 5000/5 × 10e6 |
| 24 | 6/6 | n.d. | 0/6 | 1000/10e6 |
| 96 | 12/12 | n.d. | 0/12 | 500/5 × 10e5 |
| 96 | 12/12 | n.d. | 0/12 | 100/10e5 |
| Tumor reduction: | — | — | >4.3 log | |
| Patient 3 | | | | |
| 24 | 6/6 | 6/6 | 2/6 | 4000/4 × 10e6 |
| 24 | 6/6 | 6/6 | 1/6 | 1000/10e6 |
| 96 | 12/12 | 12/12 | 0/12 | 500/5 × 10e5 |
| 96 | 12/12 | 12/12 | 0/12 | 100/10e5 |
| Tumor reduction: | — | — | 3 log | |

[a]Number of positive wells (tumor growth) of 6 or 12 sample wells, respectively, after a culture period of 14 days MNC=Mono-nucleated cells Although it is exemplified in the following with respect to mammary carcinoma patients the procedure of the invention is not only useful for the reduction of contaminating tumor cells in stem cell preparations of mammary carcinoma patients but may for example also be employed to reduce contaminating tumor cells in stem cell preparations of ovarian cancer patients or of patients with acute or chronic leukemias, lymphomas, testicular cancer or other cancers sensitive to chemotherapy. The respective antibodies or combinations of antibodies, respectively, to be preferably used are well-known to the skilled artisan or can be selected and determined routinely by one skilled in the art without inventive step.

Thus, the subject of the treatment according to the invention is the healing or the prolongation of disease-free survival of patients suffering from mammary carcinoma and in particular of advanced mammary carcinoma by an autologous stem cell transplantation. For example, in a preferred embodiment of the invention the achievement of this subject after diagnosis of mammary carcinoma consists of the following individual steps of:

1. After diagnosis of metastasization tumor cells should be obtained—whenever possible. Detection of the antigens or antigen density of c-erb-B2 and Ep-CAM (epithelial cell adhesion molecule) antigens on native tumor cells by flow cytometry. Cryoconservation of tumor cells.
2. Preparation of autologous T lymphocytes from peripheral blood by leucophoresis prior to chemotherapy; examination of a possible tumor cell contamination of the leucophoresis product by immunohistochemistry and RT-PCR; purification of T cell concentrates from contamination with tumor cells by immunomagnetic beads.
3. Two cycles of chemotherapy according to the EC schedule (epirubicine 60 mg/m$^2$ +cyclophosphamide 600 mg/m$^2$, followed by G-CSF (5–10 μg/kg/day)), monitoring of recovery of hematopoiesis and of CD34+ cell mobilization after the cycles.
4. Preparation of hematopoietic stem cells from blood by leucophoresis after mobilization with epirubicine/cyclophosphamide chemotherapy and G-CSF whereby at least 4×10$^6$ CD34+ cells/kg should be obtained.
5. Destruction of contaminating tumor cells in the autologous stem cell preparation using bispecific antibodies (anti-CD3 x anti-c-erbB-2 and anti-CD3 x anti-Ep-CAM, 500 μg/patient) by incubation for 24–48 h at room temperature and a cell density of 30,000–50,000 cells/μl. Cryoconservation at −180° C.
6. Two cycles of chemotherapy according to the ET schedule (epirubicine 60 mg/m$^2$+taxole 175 mg/m$^2$, followed by G-CSF (5–10 μg/kg/day)), monitoring of recovery of hematopoiesis and of CD34+ cell mobilization. Optionally performance of leucophoresis for a back-up preparation.
7. 3 weeks after last inductive chemotherapy performance of myeloablative high-dose chemotherapy with thiotepa (600 mg/kg i.v.) and melphalane (160 mg/kg i.v.).
8. Subsequent reinfusion of autologous stem cells.
9. 24 h after reinfusion administration of 1 mg bsAb for restimulation of activated T cells contained in the stem cell transplant and maintenance of the anti-tumor reactivity by measures for prevention and treatment of anaphylactoid reactions. Haagen et al. were able to show in in vitro experiments that successive doses of bsAb within 3 days significantly enhance the killing of tumor cells.
10. Reinfusion of autologous T cells after hematopoietic reconstitution (approx. on day 14–21) after autologous stem cell transplantation. Monitoring of T cell reconstitution in peripheral blood by flow cytometry particularly considering the CD45RA/CD45RO ratio of the T helper cells.
11. Administration of bispecific antibodies (200 μg/1 mg/2 mg) in vivo in increasing dosage on three successive days accompanied by measures for prevention and treatment of anaphylactoid reactions.
12. Follow-up examinations: evaluation of the degree of remission, anti-antibody reaction against mouse and rat immunoglobulin; monitoring of hematopoietic recovery and of reconstitution of the T cell sub-population in peripheral blood; regular aftercare to evaluate the duration of the remission achieved. Experiments to detect tumor-specific T cells from peripheral blood.

Thus, according to the invention bispecific antibodies are employed for the reduction of the number of contaminating tumor cells for example of mammary carcinoma cells by destruction thereof in stem cell preparations. In this procedure, the antibodies function to redirect T cells to the vicinity of carcinoma cells and activate T cells to secrete cytokines such as tumor necrosis factor α, leading to lysis of the tumor cell. By activation of macrophages via the Fc receptor located in the Fc portion of the bispecific antibody this cytokine effect is even enhanced; important co-stimulatory signals could be transmitted simultaneously to the T cell from the FcγRI+ cell (monocyte/macrophage/dendritic cell) which prevent the anergizing of the T cell.

After transplantation has been performed bispecific antibodies are infused in increasing dosage following reinfusion of autologous T cells. Activation of T cells and lysis of residual mammary carcinoma cells is achieved in vivo. In this case, also tumor-specific T cells could be expanded (besides the stem cell preparation mentioned under 1) which up to then have been anergic due to partial stimulation at the tumor site via the T cell receptor without co-stimulus or due to IL-10 secretion by the tumor, respectively.

According to present knowledge, the immunotherapy is only able to develop its complete effectivity against autologous tumors in the stage of a negligible residual disease; the combination of immunotherapy with high-dose chemotherapy and autologous stem cell transplantation seems to be most promising. For this reason, the T cells should not be infused after termination of chemotherapy or radiotherapy, respectively.

The preparation of bispecific antibodies is well known in the prior art. For example, intact bispecific antibodies may be produced in sufficient amounts using a newly developed method of preparation (2). The combination of two bispecific antibodies directed against two different tumor-associated antigens (e.g. c-erb-B2, Ep-CAM, such as GA-733-2=C215) on the mammary carcinoma cells minimizes the risk that tumor cells expressing only one of the antigens remain unidentified.

The risk of reinfusion of vital tumor cells together with the T cell concentrate can be largely excluded by the purification by antibodies and immunomagnetic beads. Low amounts of residual tumor cells should be detected immunohistochemically as well as by RT-PCR for the C215 or CK19 antigen, respectively.

Because of the possible release of cytokines the bispecific antibodies are first administered in a low dosage and under strict control. According to reports in the literature similar bispecific antibodies were administered systemically in an amount of up to 13 mg without substantial side effects (1). Therefore side effects are hardly to be expected for a total amount of antibody of 4 mg/patient.

In the following the role of bispecific antibodies in the combination of chemotherapy and immunotherapy for the destruction of residual mammary carcinoma cells in the transplant and in the patient is described.

By a G-CSF treatment employed to mobilize stem cells in the periphery also the number of Fcγ-RI-positive cells is increased (3). This is mostly due to the G-CSF-induced Fcγ-RI expression on neutrophil granulocytes. The high affinity Fcγ-receptor I is able to also bind to heterologous rat/mouse bsAb of the isotype combination rat IgG2b and mouse IgG2a (4). This isotype combination has been selected for the bsAb employed herein to inhibit the binding to the lower affinity Fcγ-receptor types II and III which are much more abundant (12) and therefore minimize the risk of unregulated release of cytokins. A dose of 13 mg of a bsAb having the isotype combination rat IgG2b and mouse IgG1 showing a similar behavior has already been tested in patients during a phase I study. There were few toxic side effects (grade I in the WHO classification scale) (13) so that the projected dose of 4 mg/patient should be well tolerated.

Binding of the bsAb to Fcγ-RI shows two essential advantages with regard to an optimal anti-tumor effectivity:
1. Fcγ-RI-positive cells have the ability to eliminate tumor cells by ADCC (3) and, thus, are able to contribute synergistically to the anti-tumor effect of the cytotoxic T cells directed to the tumor by the bsAb (5).
2. FcγRI-positive cells (such as monocytes/macrophages/dendritic cells) are able to provide important co-stimulatory signals similar to antigen presentation to the T cell and, thereby, prevent anergizing of the T cell. Furthermore, as shown in FIG. 1, even T cells having a T cell receptor which recognizes tumor-specific peptides (presented via MHC antigens on the tumor cell) can be stimulated as a desired byproduct due to the interaction of the T cell with accessory cell and tumor cell mediated by intact bsAb. In this constellation, the co-stimuli neccessary for correct activation of the T cell would be provided by the accessory cell (such as the monocyte). Thus, besides the direct T cell receptor-independent bsAb-mediated tumor killing (FIG. 1A) the approach presented herein should also be able to activate and generate tumor-specific T cells (FIG. 1B) which after degradation of the bsAb continue to patrol in the patient. That means, similar to genetherapeutic approaches (e.g. by incorporation of co-stimulatory antigens such as B-7 in the tumor cell) by intact bsAb the tumor tolerance in the patient can be reversed. The results of experiments performed with the syngeneic animal model shown in Example 1 are supportive of this hypothesis.

In this respect it is further advantageous that the expression of Fcγ-RI on the respective cells is up-regulated after G-CSF treatment and the circulation time of bsAb with Fc portion is significantly longer than for example of bsF(ab')2 or bs(scFv) antibody fragments so that considerably lower doses of intact ab molecules are required to achieve a comparable anti-tumor effect.

The therapy approach presented herein is aimed to the killing of residual tumor cells/micrometastases. In the treatment of solid tumors or larger metastases the above-mentioned antibody fragments may be advantageous since they allow for better penetration of the tumor due to their smaller size, whereas intact bsAb with their well known Fc portion-dependent effector mechanisms are preferable in the case of micrometastasization.

It is further advantageous that with the application schedule presented herein (up to two days of in vitro incubation of the autologous PBSZ with 500 μg of bsAb) no anti-antibodies which might inhibit the therapy are to be expected. Since after autologous stem cell transplantation the patient is in an immune-suppressed state it may be assumed that anti-antibodies against the bsAb administered 2 weeks after transplantation in combination with the autologous T cells do not yet exist.

No negative effects of the immunotherapy using bsAb on the growth of the autologous stem cells have to be expected due to the antibody specificities selected.

Further, intact bsAb may be produced by fusion of rat and mouse hybridomas and subsequent one-step purification via protein A in a cost effective manner and in clinically relevant amounts.

REFERENCES

1. Weiner & De Gast, Bispecific monoclonal antibody therapy of B-cell malignancy, *Leukaemia and Lymphoma*, 1995, 16:199
2. Lindhofer et al, Preferential species-restricted heavy-light chain pairing in rat-mouse quadromas: Implications for a single step purification of bispecific antibodies, *J. Immunology* 1995, 155:219
3. Valerius et al., Involvement of the high-affinity receptor for IgG (FcgRI; CD64) in enhanced tumor cell cytotoxicity of neutrophils during granulocyte colony-stimulating factor therapy, *Blood*, 1993, 82:931–939
4. Haagen et al., Interaction of human monocyte Fcg receptors with rat IgG2b, *J.Immunology.*, 1995, 154: 1852–1860
5. Weiner et al., The role of T cell activation in anti-CD3 x antitumor bispecific antibody therapy, *J. Immunology*, 1994, 152:2385
6. Kaneko et al. Combination of IL-2 stimulated lymphocytes and bispecific antibodies that efficiently lyse leukemic cells does not affect bone marrow CD34-positive stem cell function in vitro. *Bone Marrow Transpl.*1994, 14:213
7. Gale et al. Autotransplants in leukemia. *Lancet* 1989, ii:315
8. Gribben et al. Immunologic purging of marrow assessed by PCR before autologous BMT for B cell lymphoma. *New Engl. J. Med.* 1991, 325:1525

We claim:

1. A method for the reduction of the number of contaminating tumor cells in stem cell transplants ex vivo, comprising contacting stem cell transplants with intact bispecific antibodies capable of binding to the T cell receptor complex of a T cell, to the Fc-receptor of a Fc-receptor positive cell as well as to tumor-associated antigens on a tumor cell, under conditions that allow said binding of said bispecific antibody to said tumor cells, T cells and Fc-receptor positive cells, activation of said T cells by said antibody binding, binding of said Fc-receptor positive cells to the Fc-region of said bispecific antibody redirection of said T cells and Fc-receptor positive cells to said tumor cells, destruction of said tumor cells by said activated T cells, and ADCC killing of said tumor cells by said Fc-receptor positive cells.

2. Method according to claim 1 in which said stem cell transplants are from patients suffering from a cancer selected from the group consisting of mammary carcinoma, ovarian carcinoma, and leukemia.

3. Method according to claim 1 in which said bispecific antibodies are members selected from the group consisting of anti-CD3 X anti-c-erbB-2antibodies, anti-CD3 X anti-Ep-CAM antibodies, and anti-CD3 X anti-Lewis Y antibodies.

4. Method according to claim 1 in which said stem cell transplant is contacted with the bispecific antibodies for a period of 4–72 hours.

5. Method according to claim 4 in which said stem cell transplant is contacted with said bispecific antibodies at a temperature of 20–25° C.

6. Method according to claim 1 in which the cells in the stem cell transplant are present in a density of 30,000 to 75,000 cells per μl.

7. Method according to claim 1, in which the Fc-receptor positive cell is a member selected from the group consisting of a monocyte, a macrophage, and a dendritic cell.

8. Method according to claim 1 in which said stem cell transplants are obtained from patients selected from the group consisting of female patients with mammary carcinoma, female patients with ovarian carcinoma, patients with acute or chronic leukemia, patients with lymphomas, patients with testicular carcinoma, and patients with carcinomas sensitive to chemotherapy.

9. Method according to claim 1 in which said stem cell transplant is contacted with the bispecific antibodies for a period of 24–48 hours.

10. Method according to claim 4 in which said stem cell transplant is contacted with said bispecific antibodies at room temperature.

* * * * *